United States Patent [19]

Apesteguia et al.

[11] Patent Number: 5,508,246
[45] Date of Patent: Apr. 16, 1996

[54] CATALYSTS FOR ISO-ALCOHOL SYNTHESIS FROM CO+$H_2$

[75] Inventors: Carlos R. Apesteguia, Santa Fe, Argentina; Stuart L. Soled; Sabato Miseo, both of Pittstown, N.J.

[73] Assignee: Exxon Research and Engineering Company, Florham Park, N.J.

[21] Appl. No.: 341,773

[22] Filed: Nov. 18, 1994

Related U.S. Application Data

[63] Continuation of Ser. No. 60,172, May 7, 1993, Pat. No. 5,387,570.

[51] Int. Cl.6 .............................. B01J 21/10; B01J 23/02
[52] U.S. Cl. ........................................... 502/341; 518/717
[58] Field of Search .............................. 518/717; 502/341

[56] References Cited

U.S. PATENT DOCUMENTS

| | | |
|---|---|---|
| 3,857,899 | 12/1974 | Tasaka et al. . |
| 3,947,380 | 3/1976 | Whelan et al. . |
| 4,235,799 | 11/1980 | Wentworth et al. . |
| 4,289,709 | 9/1981 | Kaiser . |
| 4,291,126 | 9/1981 | Sugier et al. . |
| 4,598,061 | 7/1986 | Schneider et al. . |
| 4,657,887 | 4/1987 | Hardman et al. . |
| 4,835,132 | 5/1989 | Sambrook . |
| 5,063,191 | 11/1991 | Drake . |
| 5,089,532 | 2/1992 | King et al. . |
| 5,280,002 | 1/1994 | Bonneau et al. . |
| 5,321,188 | 6/1994 | Fornasari et al. . |
| 5,387,570 | 2/1995 | Apesteguia et al. ............ 502/304 |

OTHER PUBLICATIONS

C. M. Hay, et al., "Activation of Copper–Cerium Intermettallic Catalyst Precursors by Temperature–Programmed Oxidation," Applied Catalysis, 37 (1988) pp. 291–304.

Wilhelm Keim, et al., "Isobutanol From Synthesis Gas," Catalysis Letters 3 (1989) pp. 59–64.

"Methanol Synthesis Activity of Au/$CeO_2$ Catalysts Derived from a $CeAu_2$ Alloy Precursor: Do Schottky Barriers Matter?" J. of Catalysis 134, 747–750 (1992).

Kushihashi et al., "Direct Formation of Ketones and Secondary Alcohols," J. Chem. Soc. Chem. Commun., 1992, (3), 259–60.

Stiles et al., "Catalytic Conversion of Synthesis Gas to Methanol and Other Oxygenated Products," Ind. Engl. Chem. Res., 1991, 30, 811–821.

Kushihashi et al., "Direct Formation of Ketones and Secondary Alcohols from Carbon Monoxide Hydrogen & Water Over Cerium Oxide Catalysts", J. Chem. Soc., Chem. Commun. pp. 259–260, 1992.

Primary Examiner—Asok Pal
Attorney, Agent, or Firm—Estelle C. Bakun

[57] ABSTRACT

A new catalyst based on coprecipitated mixtures or solid solutions of alkaline earth oxides and rare earth oxides, such as mixtures or solid solutions of magnesium oxide and cerium oxide, $Mg_5CeO_x$, or magnesium oxide and yttrium oxide, $Mg_5YO_x$, which catalyze aldol condensation reactions leading to the selective formation of branched $C_4$ alcohols. The catalysts may also contain a Group IB metallic component and further an alkali dopant. Preferably, Cu in concentrations at or lower than 30 wt % and K in concentrations at or lower than 3 wt % will be used. The catalyst affords the advantage of being run at pressures lower than those required by prior art catalysts and are more active and selective to methanol and isobutanol.

7 Claims, No Drawings

CATALYSTS FOR ISO-ALCOHOL SYNTHESIS FROM CO+ $H_2$

This is a continuation of application Ser. No. 060,172, filed May 7, 1993, now U.S. Pat. No. 5,387,570.

BACKGROUND

Recently increasing research efforts have been devoted to converting syn-gas ($CO/CO_2/H_2$) to methanol and isobutanol mixtures for use as raw materials in methyltertiarybutylether synthesis (MTBE). Prior art catalysts consisted of modified methanol synthesis catalysts, such as mixtures of manganese, chromium, and (zinc) oxide promoted with alkali ($Mn(Zn)O/Cr_2O_3$/alkali) operated at high temperatures, and alkali promoted copper and zinc oxide (Cu/ZnO/alkali) operated at low temperatures. Keim et al., Catalysis Letters, 3, 59, 1989, describe a palladium supported on a coprecipitated manganese, zinc, zirconium, lithium oxide ($ZrO_2$—ZnO—MnO—$Li_2O$—Pd) catalyst which is highly active and selective for a one step synthesis of isobutanol. What is needed in the art is a catalyst capable of selectively producing methanol and isobutanol mixtures from syn-gas at lower temperatures (e.g. 290°–360° C. vs. 400° C.) and pressures (50 atm vs. 100–250 atm).

SUMMARY OF THE INVENTION

Applicants have discovered new catalysts based on coprecipitated mixtures or solid solutions of alkaline earth oxides and rare earth oxides, such as mixtures or solid solutions of magnesium oxide and cerium oxide, $Mg_5CeO_x$, or magnesium oxide and yttrium oxide, $Mg_5YO_x$, which catalyze aldol condensation reactions leading to the selective formation of branched $C_4$ alcohols. Applicants' catalysts may also contain a Group IB metallic component and further an alkali dopant. Preferably Cu in concentrations of 5 to 30 wt % inclusive, and K in concentrations of 0.5 to 3 wt % inclusive will be used. Applicants' catalysts afford the advantage of being run at pressures lower than those required by Keim catalysts and are more active and selective to methanol and isobutanol.

The present invention is directed to catalyst compositions comprising a coprecipitated mixture or a solid solution of a rare earth oxide and a Group IIA oxide.

The catalyst composition may further comprise a Group IB metal and may still further comprise an alkali dopant.

The invention is also directed to the use of the catalysts in a syn-gas conversion reaction.

DETAILED DESCRIPTION OF THE INVENTION

The catalysts of the present invention are prepared by coprecipitation of rare earth oxides and alkaline earth oxides at controlled pH. Preferably the Group IB metal will also be coprecipitated. For example copper oxide can be coprecipitated and then reduced to Cu prior to catalyst use. During the preparation of the instant catalysts, the pH will be controlled between 9–11. The catalysts are easily prepared by techniques known to those skilled in the art. The catalyst components are solutions of soluble salts, e.g. $Ce(NO_3)_3.6H_2O$ and $Mg(NO_3)_2.6H_2O$ or any other soluble salts. The solution containing the soluble salt is then mixed with a basic solution e.g. KOH to cause precipitation. This mixing of the soluble salt solution and base is performed at a pH of between 9–11. A coprecipitated solid is thus obtained. The Group IIA component may be present as a carbonate, hydroxide, or mixture of the two at this stage in the catalyst preparation depending on whether a hydroxide or carbonate solution was used as the basic solution, and whether any $CO_2$ was absorbed from the atmosphere. The catalysts are then calcined at about 350°–1000° C. to convert the Group IIA and rare earth salts into their respective oxides. The calcination temperature will depend on the particular rare earth and Group IIA salts and is readily determined by one skilled in the art. Preferably the additional Group IB metal which may also form part of the present catalyst will be simultaneously contained in the soluble salt solution and coprecipitated. When the molar ratio of rare earth oxide to Group IIA oxide is greater than about 50–80%, a solid solution forms wherein the Group IIA oxide is substituted into the rare earth oxide. For example, an atomic ratio of $5_{IIA}/1$ rare earth would yield a coprecipitated mixture and $0.5_{IIA}/1$ rare earth a solid solution. These can be easily distinguished by verifying the presence of two or one phases in the x-ray diffractogram.

Any soluble salts of the rare earths and Group IIA elements can be used to form the solutions of soluble salts for coprecipitation. For example, nitrates, acetates, halides etc. can be used, or any other salts known to those skilled in the art to form the desired product.

The catalysts of the present invention will typically comprise from about 10 to about 70 wt % of the Group IIA oxide, preferably 10 to about 30 wt %. Such Group IIA oxide can be selected from any of the Group IIA oxides of Mg, Ca, Sr, Ba, and mixtures thereof. Preferably magnesium oxide will be used.

The rare earth oxide will be present in an amount ranging from about 40 to about 90 wt %, preferably about 70 to about 90 wt %. The rare earth oxides are the oxides of the elements of the periodic table having atomic numbers 57 to 71 inclusive. Also included is yttrium, having an atomic number of 39, which behaves similar to rare earths in many applications. Preferably ceria or yttria will be used. Mixtures of the rare earth oxides may also be used.

When the catalyst composition of the present invention further comprises a metal, the metal will be selected from the Group IB elements and mixtures thereof. Preferably Cu will be used. The amount of metal will range from about 5 to 30 wt %, preferably about 5 to about 20 wt %, most preferably less than 10 wt %. Preferably, the metal will be Cu.

When the catalyst composition further comprises an alkali dopant, such dopant will be selected from the elements of Group IA of the periodic table (Kirk-Othmer, Encyclopedia of Chemical Technology, 2nd ed., 1965, pg 94), Li, Na, and K. Preferably potassium will be used. The alkali dopant will be present in an amount ranging from about 0.5 to about 3 wt %, preferably about 0.5 to about 1.5 wt %, and most preferably less than 1 wt %. As used herein, alkali dopant means a Group IA alkaline element added to the catalyst.

The catalysts of the present invention are particularly useful for converting synthesis gas to oxygenates, especially methanol and isobutanol. Isobutanol is a key intermediate reactant for the synthesis of methyltertiarybutylether (MTBE). MTBE has become increasingly important for use in low emissions gasoline.

The catalysts of the present invention convert synthesis gas (syn-gas), which comprises carbon monoxide, carbon dioxide and hydrogen, into oxygenates. Predominantly methanol and isobutanol are formed, while some other linear alcohols, branched alcohols, dimethylether, and esters are also formed as by-products.

A typical conversion of syn-gas is conducted at temperatures ranging from about 260° to about 420° C., pressures of 50 to about 250 atm, and GHSV 1000 to 5000 CC(STP)/g cat. hr. The $H_2$:CO molar ratio ranges from about 2 to about 0.5, preferably an $H_2$:CO ratio of 1 will be used. The present invention catalyst is advantageous because it can also selectively produce isobutanol and methanol at lower pressures of 20–50 atmospheres in addition to pressures of 50 to about 250 atmospheres. The present invention catalyst will preferably be run at pressures of 20–50 atmospheres with other conditions being those of a typical syn-gas conversion reaction.

The syn-gas conversion to alcohols can be represented by the reactions $$2nH_2 + nCO \rightarrow C_nH_{2n+1}OH + (n-1)H_2O$$

$$(n+1)H_2 + (2n-1)CO \rightarrow C_nH_{2n+1}OH + (n-1)CO_2$$

specifically, isobutanol production is represented by the reactions $$8H_2 + 4CO \rightarrow C_4H_9OH + 3H_2O$$

$$5H_2 + 7CO \rightarrow C_4H_9OH + 3CO_2$$

The catalysts of the present invention can be used for selectively producing methanol and isobutanol mixtures from syn-gas at lower temperatures and pressures (e.g. 290° C.–360° C. vs 400° C. and 20–250 atms vs. 100–250 atm, respectively). The higher temperature and pressures are what is typically required for prior art catalysts.

The following examples are illustrative of the invention but not limiting.

EXAMPLE 1

Several catalysts were prepared, including Keim type catalyst for comparison with the catalysts of the instant invention. The supported catalysts are designated by a slash, e.g., $Cu/M_\alpha M_\beta O_x$ designates a supported copper catalyst where Cu is in wt % and $\alpha$ and $\beta$ are gm atom quantities. Coprecipitated catalysts are designated without a slash, e.g., $Cu_z M_\alpha M_\beta O_x$ where z, $\alpha$, and $\beta$ are gm atom quantities. Note that the rare earth and Group IIA oxides designated by M' and M are always coprecipitated and the slash or absence thereof indicates whether the alkali dopant or Group IB metal is supported or the Group IB is coprecipitated. x is easily calculated by one skilled in the art by multiplying the valence of each cation by the number of gm atoms and dividing by (the valence of oxygen=2), e.g. $Cu_{0.5}Mg_5CeO_x$ with $Cu^{+2}$, $Mg^{+2}$, $Ce^{+4}$, x=(1+10+4)/2=7.5.

7%Cu/CeO$_2$ (7% copper supported on ceria)

41 gm of $Ce(NO_3)_3.6H_2O$ was dissolved in 200 cc $H_2O$. 35 cc of 14.8 molar $NH_4OH$ was dissolved in 200 cc of $H_2O$ and added to the cerium nitrate solution until the pH reached 9.5. The precipitate is filtered, washed with water and dried at 100° C. overnight. The material is then calcined at 500° C. overnight to convert to $CeO_2$. 2.7 gms of $Cu(NO_3)_2.H_2O$ was dissolved in 3 cc of $H_2O$ and impregnated onto 10 grams of the $CeO_2$, which was then dried overnight at 110° C. and calcined at 450° C. for four hours.

$Cu_{0.5}Mg_5CeO_x$ (coprecipitated copper, magnesium oxide, and ceria)

A one liter aqueous solution (A) containing 197.4 gm of $Mg(NO_3)_2.6H_2O$, 66.9 gm of $Ce(NO_3)_3.6H_2O$ and 18.4 gm of $Cu(NO_3)_2.3H_2O$ was prepared. A second one liter aqueous solution (B) containing 120.8 gm of KOH and 10.8 gm of $K_2CO_3$ was also prepared. The two solutions were added to 400 cc of water kept at 65°–70° C. contained in a 4 liter beaker. 15 cc/min of solution A was added by a pump into the 4 liter beaker. The simultaneous addition of solution (B) was controlled so that the pH of the well stirred mixture was maintained at 9. After solution (A) was exhausted, the resulting precipitate was filtered, washed with hot water and dried at 80° C. overnight. The catalyst was then calcined at 450° C. for four hours.

0.9% $K/Cu_{0.5}Mg_5CeO_x$ (potassium supported on coprecipitated copper, magnesium oxide, and ceria)

9.91 grams of the calcined catalyst above was taken. 0.16 gm of $K_2CO_3$ was dissolved in 8 cc of water and impregnated by incipient wetness. The catalyst was then calcined at 450° C. for four hours.

0.25% $Pd/ZrZnMnO_x$ (Keim type)

A one liter aqueous solution (A) containing 202.4 gm of $ZrO(NO_3)_2.4H_2O$, 198.4 gm of $Zn(NO_3)_2.6H_2O$ and 238.6 gm of a 50% aqueous solution of manganese nitrate was prepared. A second one liter aqueous solution (B) containing 168.0 gm of lithium hydroxide was also prepared. The two solutions were added to 400 cc of water kept at 65°–70° C. contained in a 4 liter beaker. 15 cc/min of solution (A) was added by a pump into the 4 liter beaker. The simultaneous addition of solution (B) was controlled so that the pH of the well stirred mixture was maintained at 11. After solution (A) was exhausted, the resulting precipitate was filtered, washed with hot water and dried at 120° C. overnight.

100 gm of the washed and 120° C. dried precipitate preparation above was taken. 5 cc of a palladium solution (0.05 gm Pd/cc) was added to 20 cc of water and impregnated to the point of incipient wetness, dried at 110° C., and then calcined at 330° C. for 3 hours. All catalysts were reduced in 100% $H_2$ for four hours at 260° C. before use.

7% $Cu/Mg_5YO_x$ copper supported on magnesium oxide, and yttria

A one liter aqueous solution (A) containing 106.9 gm of $Mg(NO_3)_2.6H_2O$, and 31.8 gm of $Y(NO_3)_3.6H_2O$ was prepared. A second one liter aqueous solution (B) containing 60.8 gm of KOH and 5.8 gm of $K_2CO_3$ was also prepared. The two solutions were added to 600 cc of water kept at 65°–70° C. contained in a 4 liter beaker. 15 cc/min of solution A was added by pump into the 4 liter beaker. The simultaneous addition of solution (B) was controlled so that the pH of the well stirred mixture was maintained at 9. After solution (A) was exhausted, the resulting precipitate was filtered, washed with hot water and dried at 80° C. overnight. The catalyst was then calcined at 450° C. for four hours.

2.7 gm of $Cu(NO_3)_2.3H_2O$ was dissolved in 3 cc of $H_2O$ and impregnated onto 10 gm of the $Mg_5YO_x$ by incipient wetness, and then dried at 110° C. and calcined at 450° C. for 4 hours.

$Cu_{.45}YCeMgO_x$ coprecipitated copper, yttria, ceria, magnesium oxide

A one liter aqueous solution (A) containing 37.2 gm of $Mg(NO_3)_2.6H_2O$, 15.7 gm of $Cu(NO_3)_2.3H_2O$, 63.0 gm of $Ce(NO_3)_3.6H_2O$, and 55.5 gm of $Y(NO_3)_3.6H_2O$ was prepared. A second one liter aqueous solution (B) containing 72.4 gm of KOH and 20.0 gm of $K_2CO_3$ was also prepared. The two solutions were added to 600 cc of water kept at 65°–70° C. contained in a 4 liter beaker. 15 cc/min of solution (A) was added by a pump into the 4 liter beaker. The simultaneous addition of solution (B) was controlled so that the pH of the well stirred mixture was maintained at 9. After solution (A) was exhausted, the resulting precipitate was filtered, washed with hot water and dried at 80° C. overnight. The catalyst was then calcined at 450° C. for four hours. $Cu_{.45}NdCeMgO_x$ coprecipitated copper, neodymium oxide, ceria and magnesium oxide A one liter aqueous solution (A) containing 37.2 gm of $Mg(NO_3)_2 \cdot 6H_2O$, 15.7 gm of $Cu(NO_3)_2 \cdot 3H_2O$, 63.90 gm of $Ce(NO_3)_3 \cdot 6H_2O$, and 60.9 gm of $Nd(NO_3)_3 \cdot 5H_2O$ was prepared. A second one liter aqueous solution (B) containing 72.4 gm of KOH and 20.0 gm of $K_2CO_3$ was also prepared. The two solutions were added to 600 cc of water kept at 65°–70° C. contained in a 4 liter beaker. 15 cc/min of solution (A) was added by a pump into the 4 liter beaker. The simultaneous addition of solution (B) was controlled so that the pH of the well stirred mixture was maintained at 9. After solution (A) was exhausted, the resulting precipitate was filtered, washed with hot water and dried at 80° C. overnight. The catalyst was then calcined at 450° C. for four hours. Catalyst Reaction Testing Three grams of catalyst sized to 30/60 mesh was mixed with a quantity of quartz chips (30–60 mesh) diluent such that the total catalyst volume equals 18 cc. This charge was loaded into a fixed bed reactor of 0.37" inner diameter. All catalysts were reduced under 100% $H_2$ by raising the reactor temperature at 0.5 deg/min to 260° C. and holding at that temperature for 4 hours. The reactor was then depressurized and the 1:1 $H_2$/CO feed was introduced at 245° C. at atmospheric pressure. The pressure was raised to 50 atmospheres, the space velocity and temperatures adjusted to the values indicated in the examples, and the products monitored by on-line gas chromatography. The data indicated in the tables was measured 70–110 hours into the run.

Table 1 shows high $CH_3OH$ and isobutanol productivity for catalysts of the present invention.

TABLE 1

| PRODUCT | 7% $Cu/Mg_5YO_x$ (320° C.) | | $Cu_{.5}Mg_5CeO_x$ (290° C.) | | $Cu_{.5}Mg_5CeO_x$ (320° C.) | | 0.9% K/ $Cu_{.5}Mg_5CeO_x$ (320° C.) | | $Cu_{.45}YCeMgO_x$ (290° C.) | | $Cu_{.45}NdCeMgO_x$ (290° C.) | |
|---|---|---|---|---|---|---|---|---|---|---|---|---|
| | Sel (% C) | Prod (g/kg/h) | Sel (% C) | Prod (g/kg/h) | Sel (% C) | Prod (g/kg/h) | Sel (% C) | Prod (g/kg/h) | Sel (% C) | Prod (g/kg/h) | Sel (% C) | Prod (g/kg/h) |
| Methanol | 42.53 | 60.76 | 70.72 | 147.55 | 48.41 | 63.98 | 57.19 | 66.82 | 83.15 | 128.80 | 82.57 | 144.52 |
| Ethanol | 2.83 | 2.90 | 1.48 | 2.22 | 0.81 | 0.77 | 1.87 | 1.45 | 1.09 | 1.21 | 0.51 | 0.64 |
| 1-Propanol | 2.59 | 2.32 | 2.02 | 2.63 | 1.24 | 1.02 | 2.64 | 1.84 | 1.32 | 1.28 | 0.65 | 0.71 |
| 1-Butanol | 0.38 | 0.32 | 0.17 | 0.21 | 0.10 | 0.07 | 0.28 | 0.17 | 0.15 | 0.13 | 0.10 | 0.11 |
| Isobutanol | 5.26 | 4.35 | 8.22 | 9.92 | 9.25 | 7.07 | 10.44 | 7.16 | 5.92 | 5.30 | 8.16 | 8.26 |
| 1-Pentanol | 0.22 | 0.17 | 0.20 | 0.23 | 0.45 | 0.33 | 0.68 | 0.31 | 0.19 | 0.16 | 0.28 | 0.27 |
| 2m-1-butanol | 0.08 | 0.54 | 0.98 | 1.12 | 0.58 | 0.42 | 1.17 | 0.71 | 0.60 | 0.51 | 0.76 | 0.74 |
| Hexanol | 0.19 | 0.26 | 0.09 | 0.10 | 0.26 | 0.18 | 0.19 | 0.11 | 0.10 | 0.08 | 0.06 | 0.06 |
| DME | 1.31 | 0.41 | 3.35 | 5.02 | 2.97 | 2.82 | 1.16 | 1.04 | 0.40 | 0.45 | 1.64 | 2.07 |
| Methane | 18.62 | 13.30 | 8.38 | 8.7 | 20.06 | 13.19 | 11.52 | 6.78 | 3.26 | 2.52 | 3.70 | 3.24 |
| Higher-Hyd | 23.68 | — | 4.16 | — | 15.49 | — | 12.79 | — | 3.10 | — | 2.71 | — |
| $CO_2$ (% C) | 32.17 | | 22.53 | | 40.43 | —31.04 | | 15.41 | | 17.08 | — | |
| Alc/Hyd (% C) | 1.31 | | 6.73 | | 1.73 | | 2.94 | | 14.55 | | 14.58 | |
| CO Conv (%) | 19.9 | | 25.5 | | 21.02 | | 15.5 | | 17.6 | | 20.6 | |
| GHSV (cc/g cat.h) | 1832 | | 1832 | | 1832 | | 1832 | | 1832 | | 1832 | |

($H_2$: CO = 1   P = 50 atm)
Selectivities in % C   $CO_2$ Free basis

EXAMPLE 2

A comparison between 0.9% $K/Cu_{0.5}Mg_5CeO_x$ and 0.25% $Pd/ZrZnMnO_x$ Keim's-type catalyst was performed at 290° C., 320° C., and 360° C. and is tabulated in Table 2 below. The catalysts compared are the same catalysts as described in Example 1 (for which data is presented in Table 1, exclusive of the Keim catalyst).

TABLE 2

Comparison Between 0.9% $K/Cu_{.5}Mg_5CeO_x$ And 0.25% $Pd/ZrZnMnO_x$ Keim's-type Catalyst

| | Productivity (g/kg cat/h) | | | | | |
|---|---|---|---|---|---|---|
| | 0.9% $K/Cu_5Mg_5CeO_x$ | | | 0.25% $Pd/ZrZnMnO_x$ | | |
| Product | (290° C.) | (320° C.) | (360° C.) | (290° C.) | (320° C.) | (360° C.) |
| Methanol | 144.5 | 66.8 | 30.7 | 21.2 | 40.2 | 20.5 |
| Isobutanol | 5.7 | 7.2 | 7.5 | 0.3 | 1.1 | 3.5 |

TABLE 2-continued

Comparison Between 0.9% K/Cu$_5$Mg$_5$CeO$_x$
And 0.25% Pd/ZrZnMnO$_x$ Keim's-type Catalyst

| | Productivity (g/kg cat/h) | | | | | |
|---|---|---|---|---|---|---|
| | 0.9% K/Cu$_5$Mg$_5$CeO$_x$ | | | 0.25% Pd/ZrZnMnO$_x$ | | |
| Product | (290° C.) | (320° C.) | (360° C.) | (290° C.) | (320° C.) | (360° C.) |
| Total Alcohols | 154.9 | 79.6 | 39.2 | 21.7 | 41.7 | 27.0 |
| Alcohols/Hydroc | 11.14 | 2.94 | 0.66 | 6.06 | 3.32 | 0.71 |
| CO Conv (%) | 19.9 | 15.5 | 19.0 | 2.8 | 6.9 | 10.8 |

Selectivities in % C; CO$_2$-free basis
H2/CO = 1; P = 50 atm; GHSV = 1832 cc(STP)/[(g cat).h]

This example shows that K-promoted coprecipitated copper, magnesium and cerium oxides provide higher productivity and better selectivity to isobutanol than Keim's catalysts when compared at low pressure (50 atmospheres and varying temperatures (290°–360° C.)) conditions.

EXAMPLE 3

The Cu$_{0.5}$Mg$_5$CeO$_x$ catalyst of Example 1 was tested at five different temperatures and the results are tabulated in Table 3. Increasing temperatures increases the isobutanol formation rate while methanol yield decreases due to thermodynamic equilibrium constraints. Thus, the isobutanol to methanol ratio increases at higher temperatures. However, the production of CO$_2$, methane, and higher hydrocarbons also increase at higher temperatures.

TABLE 3

Catalyst: Cu$_5$Mg$_5$CeO$_x$
Selectivities in % C (CO$_2$-free basis)
P = 50 atm; GHSV = 1832 cc/g cat.h; H$_2$:CO = 1

| Temp (°C.) | CH$_3$OH | Isobutanol | LALC | CH4 | C$_2$(+) |
|---|---|---|---|---|---|
| 260 | 89.0 | 2.6 | 3.2 | 2.6 | 0.01 |
| 275 | 81.7 | 5.0 | 3.9 | 4.6 | 0.9 |
| 290 | 70.6 | 8.2 | 4.1 | 8.4 | 4.1 |
| 320 | 50.2 | 9.6 | 3.0 | 18 | 14 |
| 360 | 23.6 | 9.8 | 2.3 | 26 | 31 |

C$_2$(+): All hydrocarbons except methane
LALC: C$_2$ to C$_6$ linear alcohols

EXAMPLE 4

The 0.9% K/Cu$_{0.5}$Mg$_5$CeO$_x$ catalyst of Example 1 was tested at several different space velocities.

Table 4 shows the effect of contact time. Long contact times favored isobutanol and branched alcohols production (terminal products) while decreasing methanol slightly (primary product); linear alcohols (ethanol, propanol, and butanol) did not change appreciably (intermediate products). Hence, selectivities can be somewhat controlled by the temperature and space velocity of the reaction.

TABLE 4

Catalyst: 0.9% K/Cu$_5$Mg$_5$CeO$_x$
Alcohol Fraction, Selectivities in % C
T = 290° C.; P = 50 atm; H$_2$:CO = 1

| GHSV (cc/g.h) | CH$_3$OH | Iso-butanol | Etha-nol | Pro-panol | 2ml-Butanol | Butanol |
|---|---|---|---|---|---|---|
| 1850 | 89.0 | 5.8 | 1.7 | 2.2 | 0.1 | 0.7 |
| 920 | 85.8 | 8.5 | 1.6 | 2.3 | 0.2 | 1.0 |
| 460 | 81.7 | 12.1 | 1.5 | 2.3 | 0.2 | 1.3 |

EXAMPLE 5

Effect of the Support in Cu-containing catalysts

Three catalysts were prepared, as detailed in Example 1, to determine the effect of the support in Cu-containing catalysts.

TABLE 5

| | Oxygenate fraction. Selectivities (in % C) | | | | | |
|---|---|---|---|---|---|---|
| | 290° C. | | | 320° C. | | |
| Oxygenates | A | B | C | A | B | C |
| Methanol | 84.38 | 79.05 | 87.3 | 69.2 | 74.2 | 74.6 |
| Ethanol | 7.24 | 1.66 | 1.71 | 7.40 | 1.23 | 2.40 |
| Propanol | 3.23 | 2.25 | 2.13 | 6.14 | 1.90 | 3.39 |
| Butanol | 0.50 | 0.19 | 0.11 | 0.86 | 0.15 | 0.35 |
| Isobutanol | 2.30 | 9.19 | 5.69 | 10.24 | 14.17 | 13.40 |
| 2-m-1-butanol | 0.40 | 1.08 | 0.73 | 1.94 | 0.90 | 1.51 |
| Others | 1.95 | 6.64 | 2.33 | 4.19 | 7.47 | 3.18 |
| Total alcohols productivity | 99.2 | 164.6 | 162.2 | 75.01 | 76.01 | 77.92 |
| Isobutanol productivity | 1.50 | 9.92 | 5.68 | 5.14 | 7.07 | 7.16 |
| Branched/Linear alcohols ratio | 1.50 | 2.56 | 1.73 | 0.85 | 3.69 | 2.18 |
| CO conv (%) | 12.8 | 25.5 | 20.4 | 16.4 | 21.02 | 15.5 |
| Alc/Hyd (% C) | 8.5 | 6.03 | 15.2 | 2.61 | 1.63 | 2.94 |

Productivities, in g/kg cat/h
P = 50 atm; H$_2$/CO = 1: T = 320° C.; GHSV = 1832 cc(STP)/[(g cat).h]

Example 5 illustrates the effect of the support on Cu-containing catalysts. At 290° C., Cu supported on CeO$_2$ produced a low selectivity to isobutanol and the major products in the oxygenate fraction other than methanol were ethanol and propanol. At 320° C. the selectivity to isobutanol increased to 10.2% but the production of linear alcohols was still significant giving a branched/linear alcohols ratio of 0.85. When copper oxide was coprecipitated with magnesia and ceria and then reduced, as in $Cu_{0.5}Mg_5CeO_x$, the activity, selectivity, and productivity to isobutanol increased dramatically. Compared with the 7% $Cu/CeO_2$ catalyst at 290° C., CO conversion increased from 12.8 to 25.5%, isobutanol selectivity from 2.3 to 9.19% and isobutanol productivity from 1.50 to 9.92 g/kg cat/h. At 320° C., $Cu_{0.5}Mg_5CeO_x$ remained more active and selective to isobutanol than 7% $Cu/CeO_2$. The gain in isobutanol productivity was accompanied by a simultaneous diminution of the formation of linear alcohols and, as a consequence, the branched/linear alcohols ratio increased from 0.85 (Catalyst A) to 3.69 (Catalyst B). Adding K to Catalyst B produced a less active catalyst; however, the presence of an alkali dopant diminished the formation of hydrocarbons and dimethylether. For example, the alcohol/hydrocarbon ratio increased from 1.63 (Catalyst B) to 2.94 (Catalyst C) at 320° C. Finally, at 320° C. the 0.9% $K/Cu_{0.5}Mg_5CeO_x$ catalyst gives similar isobutanol yield compared to the undoped catalyst and higher selectivity to alcohol formation.

What is claimed is:

1. A syn-gas conversion process, having increased selectivity to methanol and isobutanol and conducted under syn-gas conversion conditions at pressures of about 20 to about 250 atmospheres, comprising contacting a carbon monoxide and hydrogen feedstream with a catalyst composition consisting essentially of a solid solution or a coprecipitated mixture of a first oxide and a second oxide, wherein said first oxide is selected from the group consisting of yttria, rare earth oxides and mixtures thereof and wherein said second oxide is a Group IIA oxide, and a Group IB metal.

2. A syn-gas conversion process according to claim 1 wherein said pressure is about 20 to about 50 atmospheres.

3. The process of claim 1 wherein said Group IB metal is copper.

4. The process of claim 1 wherein said catalyst further contains an alkali depart selected from the group consisting of Group IA elements and mixtures thereof.

5. The process of claim 1 wherein said Group IIA oxide is magnesium oxide.

6. The process of claim 1 wherein said rare earth oxide is selected from the group consisting of ceria, neodymium oxide and mixtures thereof.

7. The process of claim 1 wherein the temperature is about 290° C. to about 360° C.

* * * * *